United States Patent [19]
Auman et al.

[11] Patent Number: 5,145,999
[45] Date of Patent: Sep. 8, 1992

[54] PERFLUOROALKYLATED AMINES, AND POLYMERS MADE THEREFROM

[75] Inventors: Brian C. Auman, Newark; David P. Higley, Wilmington; Kirby V. Scherer, Hockessin, all of Del.

[73] Assignee: E. I. Du Pont de Nemours and Company, Wilmington, Del.

[21] Appl. No.: 680,486

[22] Filed: Apr. 4, 1991

[51] Int. Cl.$^5$ .................. C07C 211/45; C07C 211/56
[52] U.S. Cl. ...................................... 564/442; 548/418
[58] Field of Search ......................................... 564/442

[56] References Cited
FOREIGN PATENT DOCUMENTS 1-180860 7/1989 Japan .
1-190652 7/1989 Japan .
2-60933 3/1990 Japan .

OTHER PUBLICATIONS

C.A. 109:149040q, (1988), Nakayama, et al.
C.A. 108:94127v, (1980), Ikeda, et al.

Primary Examiner—Joseph Paul Brust

[57] ABSTRACT

1-[2,2-bis(trifluoromethyl)-3,3,4,4,5,5,5-heptafluoropentyl]-3,5-diaminobenzene and 1-[2,2-bis(trifluoromethyl)-3,3,4,4,5,5,5-heptafluoropentyl]-4-aminobenzene, as well as fluorinated polymers, preferably polyimides. The perfluoroalkyl group of these amines is connected to the benzene ring through a tertiary carbon atom followed by a methylene group. This renders the amines more reactive than other amines, where the perfluoroalkyl group is connected directly to the benzene ring. The absence of hydrogen from the group containing the tertiary carbon atom which is adjacent to the perfluorinated groups, prohibits dehydrofluorination.

2 Claims, No Drawings

PERFLUOROALKYLATED AMINES, AND POLYMERS MADE THEREFROM

1. FIELD OF THE INVENTION

This invention relates to perfluoroalkylated amines, and more particularly to 1-[2,2-bis(trifluoro-methyl)-3,3,4,4,5,5,5-heptafluoropentyl]-3,5-diaminobenzene and 1-[2,2-bis(trifluoromethyl)-3,3,4,4,5,5,5-heptafluoropentyl]-4-aminobenzene, as well as fluorinated polymers, preferably polyimides, made therefrom.

2. BACKGROUND OF THE INVENTION

Polyimides represent an important class of hightemperature polymers with a broad range of applications. In the electronics industry, they are used in many applications which take advantage of their thermal stability, good electrical properties and other very useful characteristics. Polyimides, however, tend to absorb moisture, which results in changes in electrical properties under varied humidity conditions. Additionally, as the drive in electronics for smaller size continues, materials with improved dielectric properties, e.g., lower dielectric constant, are required.

Fluorination has been used to reduce both moisture absorption and dielectric constant in polyimides. For example, Japanese Patent Application Publication (Kokai) No. 1-190652 (Appl. No. 63-12660), Japanese Patent Application Publication (Kokai) No. Hei 2-60933 (Appl. No. 63-211799), and Japanese Patent Application Publication (Kokai) No. Hei 1-18860 (Appl. No. 63-4760) disclose use of perfluoroalkyl-diaminobenzene in preparing polyimides. However, the raw materials for preparing such diamines are not readily available, and thus, it is not easy to prepare these compounds, especially in pure state without the presence of undesirable homologues. Another disadvantage of these compounds is that their reactivity is very low, due to the electron withdrawing power of the pendant perfluorinated group, which is directly connected to the benzene ring. Removal of the direct connection of the perfluorinated group from the benzene ring through the introduction of one or more intermediate methylene groups is undesirable, since the thermal stability degrades due to premature dehydrofluorination.

In contrast, the perfluorinated alkyl group, according to the present invention, is connected to the benzene ring through a tertiary carbon atom followed by a methylene group. Due to the absence of hydrogen on the carbon atom adjacent to the fluorinated carbon atoms, no dehydrofluorination takes place.

3. SUMMARY OF THE INVENTION

This invention pertains to 1-[2,2-bis(trifluoromethyl)-3,3,4,4,5,5,5-heptafluoropentyl]-3,5-diaminobenzene and 1-[2,2-bis(trifluoromethyl)-3,3,4,4,5,5,5-heptafluoropentyl]-4-aminobenzene, as well as fluorinated polymers, preferably polyimides, made therefrom. More particularly, this invention relates to a composition of matter comprising the structure:

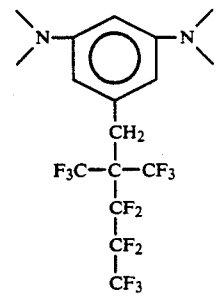

which may take the form

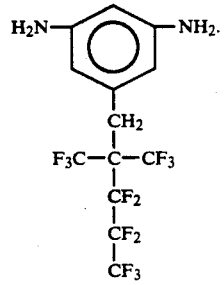

It also pertains to a composition of matter comprising repeating units of the structure:

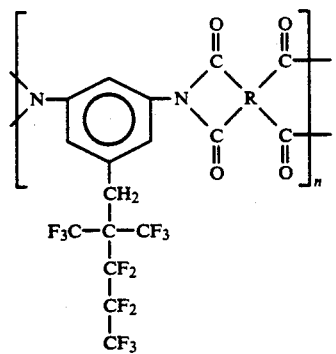

where R is a tetravalent radical, and n is an integer.

Preferably, R is

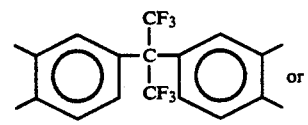

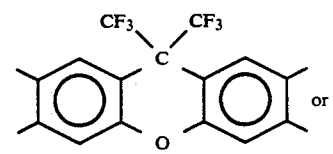

-continued

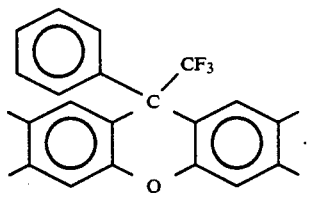

In addition, the composition of matter of this invention, may comprise the structure:

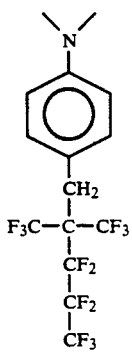

which may take the form:

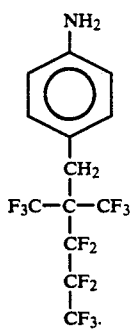

4. DETAILED DESCRIPTION OF THE INVENTION

The amines of the present invention are prepared through their respective nitro compounds, which in turn are purified, and hydrogenated to yield the corresponding amines as illustrated by the Examples cited hereinunder.

Use of the new fluorinated amines according to the present invention is an excellent route to produce new polyimides with reduced moisture absorption and dielectric constant. Likewise, other polymers based on these amines, such as for example polyamides, polyureas, and the like may be made.

1-[2,2-bis(trifluoromethyl)-3,3,4,4,5,5,5-heptafluoropentyl]-3,5-diaminobenzene may be used to form fluorinated polymers, such as for example poly(amic acids), polyamides, polyimides, polyurethanes, polyureas, and the like. It may also be used to make any other compositions of matter that diamines are suitable in being incorporated, and/or wherein the perfluoroalkyl group would be beneficial.

Although the diamines of the present invention are preferred, the corresponding monoamines, such as for example 1-[2,2-bis(trifluoromethyl)-3,3,4,4,5,5,5-heptafluoropentyl]-4-aminobenzene, are within the realm of the present invention, especially for end-capping applications, or in occasions where the molecular weight of a polymer such as a polyimide is desired to be low. Other examples of applications of the monoamine may be found in the case where a polymer having reactive pendant sites, like for example, an acrylic polymer with pendant isocyanate groups, is desired to be fluorinated. Reaction of this monoamine with the polymer will introduce pendant perfluorinated groups through urethane linkages. The preferred polymers as aforementioned are polyimides, which in this particular case, where the diamine of the present invention is employed, are usually soluble in one or more commonly used solvents, such as for example polar organic solvents, such as sulfoxide type solvents including dimethylsulfoxide, diethylsulfoxide, and the like, formamide type solvents including N,N-dimethylformamide, N,N-diethylformamide, and the like, acetamide type solvents including N,N-dimethylacetamide, N,N-diethylacetamide, and the like, pyrrolidone type solvents including N-methyl-2-pyrrolidone, N-cyclohexyl, 2-pyrrolidone, 1,3-dimethyl-2-imidozolidione, N-vinyl-2-pyrrolidone, and the like, phenolic solvents including phenol, o-, m-, p-cresol, xylenol, halogenated phenol, catechol, and the like, hexamethylphosphoramide, and a number of lactones including γ-butyrolactones. These solvents may be used alone or as a mixture. Partial use of aromatic hydrocarbons such as xylene, toluene, and the like, is also possible.

In addition, Applicants have observed that polymers with better film forming properties may result by going directly to the polyimide than by first forming the poly(amic acid) and using it for later imidization. In addition, the diamines of the instant invention are considerably more reactive than the corresponding diamines in which the pendant perfluoroalkyl group is directly connected to the benzene ring. It seems that the tertiary carbon atom followed by a methylene group between the perfluoroalkyl group and the benzene ring, in the case of the present invention, dilutes the electron withdrawing power of the perfluorinated group on the amine groups, thus affecting favorably their reactivity. Furthermore, the absence of hydrogen from the tertiary carbon group, which is adjacent to perfluorinated groups, does not give rise to dehydrofluorination.

Examples of preferable dianhydrides, which may be used with the diamines of the present invention are pyromellitic dianhydride; 2,3,6,7-naphthalene tetracarboxylic dianhydride; 1,4,5,8-naphthalene tetracarboxylic dianhydride; 3,3',4,4'-biphenyl tetracarboxylic dianhydride; 1,2,5,6-naphthalene tetracarboxylic dianhydride; 2,2',3,3'-biphenyl tetracarboxylic dianhydride; 3,3',4,4'-benzophenone tetracarboxylic dianhydride; 2,2-bis(3,4-dicarboxyphenyl)propane dianhydride; bis(3,4-dicarboxyphenyl)sulfone dianhydride; 3,4,9,10-perylene tetracarboxylic dianhydride; 1,1-bis-(2,3-dicarboxy-phenyl)ethane dianhydride; 1,1-bis-(3,4-dicarboxyphenyl)ethane dianhydride; bis-(2,3-dicarboxyphenyl)methane dianhydride; bis-(3,4-dicarboxyphenyl)methane dianhydride; oxydiphthalic dianhydride; 9-phenyl-9-trifluoromethyl)xanthene-2,3,6,7-tetracarboxylic dianhydride; 9,9-bis-(trifluoromethyl)xanthene tetracarboxylic dianhydride; 12,14-(R)$_2$-12,14-(R$_f$)$_2$-12H,14H-5,7-dioxapentacene-2,3,9,10-tetracarboxylic acid dianhydride (wherein R is selected from the group consisting of aryl, substituted aryl, and perfluoroalkyl, and $R_f$ is perfluoroalkyl); and the like.

GLOSSARY

BXDA:9,9-Bis(trifluoromethyl)-2,3,6,7-xanthenetetracarboxylic dianhydride.
CHP:N-cyclohexyl-2-pyrrolidone.
DMAC:Dimethylacetamide.
DSC:Differential Scanning Calorimetry.
6FDA:2,2'-bis(3,4-dicarboxyphenyl)hexafluoropropane.
GPC:Gel Permeation Chromatography.
mmole:1/1000 of a mole.
NMP:N-methyl-2-pyrrolidone.
PXDA:9-phenyl-9-trifluoromethyl-2,3,6,7-xanthenetetracarboxylic dianhydride
RfbMPD:1-[2,2-bis(trifluoromethyl)-3,3,4,4,5,5,5-heptafluoropentyl]-3,5-diaminobenzene.
TGA:Thermogravimetric Analysis.
THF:Tetrahydrofuran.

In the following examples, all parts and percentages are based on weight, unless otherwise stated.

EXAMPLE 1

Preparation of 3,5-Dinitrobenzyl Bromide

In a two-liter three-necked flask, equipped with a reflux condenser with gas inlet, a mechanical stirrer, and a 250-ml addition funnel, were combined under nitrogen 100.0 g (0.505 mole) of 3,5-dinitrobenzyl alcohol (Aldrich Chemical Company) and one liter of chloroform. The addition funnel was charged with a solution of 136.7 g (48.0 ml, 0.505 mole) of phosphorous tribromide in 150 ml of chloroform. This solution was added to the rapidly-stirred contents of the reaction flask during a period of three hours. Upon completion of this addition, the reaction mixture was heated at reflux for two hours, and then was left at room temperature overnight.

The organic solution was decanted from a residue of phosphorus compounds, into 1000 g of ice. The resulting mixture was transferred to a separatory funnel, and the organic was drawn off and saved. The aqueous layer was extracted with a small portion of chloroform. The combined organic solutions were washed with water, then with dilute aqueous sodium bicarbonate, and dried over anhydrous magnesium sulfate. Solvent was removed by rotary evaporation at reduced pressure to leave a solid product, m.p. 91°-94° C., which was identified by NMR spectroscopy as the desired product, 3,5-dinitrobenzyl bromide. The yield was 126.6 g (mole wt. 261.0); 0.485 mole; 96.0% of theory). A small portion of the product was recrystallized from a mixture of hexane and ethyl acetate, to obtain a purified sample with m.p. 93°-94° C.

EXAMPLE 2

Preparation of Crude 1-[2,2-bis(trifluoromethyl)-3,3,4,4,5,5,5-heptafluoropentyl]-4-nitrobenzene In a glove box containing a dry nitrogen atmosphere, a 30-g portion of spray-dried potassium fluoride (0.52 mole) was placed in a one-liter roundbottom flask, along with 76.2 g of 1-bromo-4-nitrobenzene (#16,715-0 from ALDRICH, Milwaukee, Wis.) (0.35 mole) and 500 ml of dry dimethylformamide. A magnetic stirrer bar was placed in the flask, which was then stopped and removed from the glove box. To it was then added 101 g of perfluoro-2-methyl-2-pentene (0.34 mole), and the mixture was left stirring in the flask at room temperature for twenty days.

Water was added to the flask, and its contents were transferred to a two-liter separatory funnel. The aqueous layer was discarded, and the organic layer was washed twice with water, then taken up in ether and dried over calcium chloride. The ether solvent was removed by rotary evaporation at reduced pressure to leave 147 g (0.32 mole, 95% of theory) of the crude product as a viscous amber liquid, which upon standing crystallized to a pale yellow solid.

EXAMPLE 3

Preparation of Crude 1-[2,2-bis(trifluoromethyl)-3,3,4,4,5,5,5-heptafluoropentyl]-3,5-dinitrobenzene A two-liter three-neck round-bottom flask with a magnetic stirring bar was charged in a dry atmosphere (nitrogen glove box) with 45 g (0.78 mole) of spray-dried potassium fluoride and 122.3 g (0.469 mole) of 3,5-dinitrobenzyl bromide from Example 1. The flask was capped with rubber serum stoppers and taken into the hood. A needle was inserted into one septum and under gentle nitrogen pressure, another septum was removed and 727 g of dimethylacetamide (dried by storage over 4A molecular sieve) and 160.3 g of perfluoro-2-methyl-2-pentene (0.534 mole) were added. The septum was replaced and the mixture was stirred magnetically at room temperature for 11 days.

The mixture was then worked up by slowly adding water until the flask was nearly full. [CAUTION: The mixture warms slightly and some of the excess perfluoromethylpentene may boil out.]. The mixture was allowed to stand for two days, then filtered and the filter cake was washed well with water. The crude product was a heavy granular solid, about the color and consistency of light brown sugar. After air drying, the crude product weighed 223.5 g (95.4% yield). Proton and fluorine NMR spectra were consistent with complete conversion of the starting benzyl bromide to the desired product. The crude product was then purified and hydrogenated as described in Example 5.

EXAMPLE 4

Purification and Hydrogenation of 1-[2,2-bis(trifluoromethyl)-3,3,4,4,5,5,5-heptafluoropentyl]-4-nitrobenzene The title compound, obtained in crude form Example 2, was heated with triethylamine (7.0 ml) at 80° C. for two hours, then cooled and diluted with methyl t-butyl ether. The mixture was filtered, and the filtrate was washed with 3 M HCl, then water, and dried over magnesium sulfate. The solution was filtered, and solvent removed at reduced pressure, to leave 135 g of the purified nitrobenzene derivative.

A total of 130 g of the purified material (mole wt. 455.2; 0.286 mole) was hydrogenated in four separate batches, in a glass shaker bottle, over 5% palladium on carbon, at room temperature and 60 psig hydrogen pressure. A typical batch was made up of 31 g of substrate, 3.0 g of catalyst, and 200 ml of ethanol solvent, and required about seven hours for completion of the hydrogenation. The combined hydrogenation products were filtered, and solvent was removed at reduced pressure. Distillation of the residue under vacuum afforded the pure product, 1-[2,2-bis(trifluoromethyl)-3,3,4,4,5,5,5-heptafluoropentyl]-4-aminobenzene, b.p.

98° C. (2.0 torr). The yield was 94.6 g (mole wt. 425.2; 0.222 mole, 78% of theory).

EXAMPLE 5

Purification and Hydrogenation of 1-[2,2-bis(trifluoromethyl)-3,3,4,4,5,5,5-heptafluoropentyl]-3,5-dinitrobenzene The title compound was obtained as a crude product from Example 3. Recrystallization from methanol gave 52.6 g of purified product, m.p. 81°-82.3° C.

A 27.0-g portion of the purified dinitro compound was combined in a glass pressure bottle with 200 ml of absolute ethyl alcohol and 2.7 g of 5% palladium on carbon, then shaken at room temperature under a hydrogen pressure of 60 psig for four hours. The product mixture was filtered, solvent was removed from the filtrate at reduced pressure, and the residue was recrystallized from hexane to obtain 12.3 g of purified product, 1[2,2-bis(trifluoromethyl)-3,3,4,4,5,5,5-heptafluoropentyl]-3,5-diaminobenzene, m.p. 66°-67° C. In the same manner, a 25.6-g portion of the dinitro compound was hydrogenated for about three hours over 2.6 g of 5% palladium on carbon. Isolation and recrystallization of the product as above gave 12.3 g of the diamine, m.p. 66°-66.5° C. The combined mother liquors from the recrystallizations of the two hydrogenation products yielded, upon concentration and cooling, an additional 13.2-g crop of purified product, m.p. 65°-66.5° C. From 52.6 g of the dinitro compound (mole wt. 500.2; 0.105 mole), there was thus obtained a total of 37.8 g of the diamino derivative (mole wt. 440.2; 0.086 mole; 82% of theory).

EXAMPLE 6

Into a 100 ml reaction kettle equipped with a mechanical stirrer and nitrogen inlet and outlet, were charged 3.9818 g (9.045 mmole) of RfbMPD. After dissolving the diamine in about 30 ml of NMP, 4.0182 g (9.045 mmole) of 6FDA were added as a solid with stirring. About 2 ml of NMP was used to wash in the residual 6FDA from the funnel used for addition (32 ml NMP total=20% solids W/V). The 6FDA dissolved almost immediately and the solution warmed slightly with the 6FDA addition. A moderate viscosity developed during the course of the reaction. After stirring overnight at room temperature (~18 hours), stirring was stopped and the reaction mixture was pressure filtered through a 10 micron filter. GPC analysis in DMAC containing LiBr/H$_3$PO$_4$/THF at 35° C. revealed an Mn of 82700 and an Mw of 147000 based on polystyrene which indicates high molecular weight for the poly(amic acid). Subsequently, the solution was spin coated onto silicon wafers, the wafers were prebaked at 135° C. for 30 minutes, and then placed in an air oven and heated from RT to 150° C. and held for 30 minutes, then heated to 300° C. and held for two hours. The resulting 5.2 micron polyimide film was pale yellow in color and had the following tensile properties when measured on a Instron Model 4501 at a crosshead speed of 5.080 mm/minute: tensile strength at break=65 MPa, Elongation at break=5%, Young's modulus=1.6 GPa. The film also exhibited a Tg of about 257° C. when measured on an E. I. du Pont de Nemours and Company (Wilmington, Del.) 1090 DSC at 25° C./minute. The initial weight loss temperature in air of the film by thermogravimetric analysis (TGA) was found to be about 400° C. at 15° C./minute. The linear coefficient of thermal expression by thermochemical analysis (TMA) at 10° C./minute from 0° to 200° C. was found to be 98 ppm.

EXAMPLE 7

Into a 100 ml reaction kettle equipped with a mechanical stirred and nitrogen inlet and outlet, were charged 4.0182 g (9.045 mmole) of 6FDA and 3.9817 g (9.045 mmole) of RfbMPD. The monomers were dissolved in 24 ml of NMP and allowed to react overnight at room temperature. Afterwards, the solution was cooled to 0° C. and 6.8 ml (7.36 g, 72 mmole) of acetic anhydride and 5.1 ml (5.0 g, 63.3 mmole) of pyridine were added. The solution was allowed to warm to ambient temperature and was stirred for about 8 hours at this temperature. The reaction was then diluted with acetone and precipitated into methanol. The white, fibrous polymer that resulted was then dried, redissolved in acetone and then again precipitated into methanol, followed by filtration and drying in a vacuum oven with nitrogen bleed. GPC analysis (in DMAC with 1 g/41 toluene sulfonic acid, at 135° C.) revealed an Mn=46100 and Mw=111000 versus polystyrene standards. GPC analysis in the same solvent/conditions as for the poly(amic acid) in Example 1 gave a Mn=51800 and Mw=96900 versus polystyrene. H-NMR in CDCl$_3$ at 50° C. was consistent with the proposed polyimide structure with resonances at 8.05 ppm (doublet), 7.95 ppm (singlet) and 7.85 ppm (doublet) due to the aromatic protons of 6FDA moieties, and resonances at 7.7 ppm, 7.5 ppm (aromatic, singlets) and 3.65 ppm (methylene, singlet) due to RfbMPD moieties. The Tg of this polyimide (E. I. du Pont de Nemours and Company, Wilmington, Del. 1090 DSC at 10° C./minute) was 250° C. The polymer was found to be soluble in acetone, DMAC, tetrachloroethane, butyl acetate and cyclohexanone. It gave a turbid solution in NMP and was swollen by gammabutyrolactone.

EXAMPLE 8

Into a 100 ml reaction kettle equipped with a mechanical stirrer and nitrogen inlet and outlet, were charged 6.0273 g (13.567 mmole) of 6FDA and 5.9727 g (13.567 mmole) of RfbMPD. The monomers were dissolved in 36 ml of NMP and allowed to react overnight at room temperature. Afterwards, the solution was diluted with about 12 ml NMP and then successively 10.2 ml (11.08 g, 108.54 mmole) of acetic anhydride and 7.7 ml (7.5 g, 94.97 mmole) of pyridine were added. The solution was allowed to stir for several additional hours at room temperature and then was precipitated into methanol. The white, fibrous polymer that resulted was then dried, redissolved in chloroform and then again precipitated into methanol. After drying in a vacuum oven with nitrogen bleed, the polymer was dissolved in butyl acetate (about 20 to 30% solids) and filtered through an 1 micron filter. It was then spin coated onto silicon wafers, prebaked at 135° C. in air for 30 minutes, and then heated in a nitrogen oven from room temperature to 350° C. and held at 350° C. for 1 hour. The resulting 14.6 micron, very pale yellow polyimide film had the following tensile properties when measured on a Instron Model 4501 at a crosshead speed of 5.080 mm/minute: tensile strength at break=71.9 MPa, Elongation at break=6%, Young's modulus=1.7 GPa.

EXAMPLE 9

Into a 100 ml reaction kettle equipped with a mechanical stirrer and nitrogen inlet and outlet, were charged 5.1003 g (11.13 mmole) of BXDA and 4.89977 g (11.13 mmole) of RfbMPD. The monomers were dissolved in 24 ml of NMP and allowed to react overnight at room temperature. Afterwards, 8.4 ml (9.09 g, 89 mmole) of acetic anhydride and 6.3 ml (6.44 g, 77.9 mmole) of pyridine were added successively. After several hours of reaction, polymer started to precipitate from solution and the reaction solution was then diluted with 16 ml of NMP and allowed to react for an additional 6 hours. The final reaction mixture was not homogeneous but the polymer was highly swollen by the solvent. Some acetone was added to the solution in an attempt to homogenize the solution, but the solution did not become homogeneous. The reaction mixture was then precipitated into methanol, and after filtration and drying the polymer was redissolved in chloroform and then reprecipitated into methanol. A white fibrous polymer resulted which after filtration and drying was found by GPC (in DMAC with 1 g/41 toluene sulfonic acid, at 135° C.) to have an Mn=53200 and Mw=114000 versus polystyrene standards. H-NMR in CDCl3 was consistent with the proposed polyimide structure with resonances at 8.55 ppm and 7.9 ppm due to the aromatic protons of BXDA moieties, and resonances at 7.75 ppm, 7.55 ppm (aromatic) and 3.7 ppm (methylene) due to RfbMPD moieties. Subsequently, the polymer was dissolved in tetrachloroethane (TCE) and filtered through an 1 micron filter. It was then spin coated onto silicon wafers, prebaked at 135° C. in air for 30 minutes, and then heated in a nitrogen oven from room temperature to 200° C. and held for 30 minutes and then heated to 350° C. and held at 350° C. for 1 hour. The resulting 10.5 micron, essentially colorless polyimide film had the following tensile properties when measured on an Instron Model 4501 at a crosshead speed of 5.080 mm/minute: tensile strength at break=116 MPa, Elongation at break=28%, Young's modulus=2.0 GPa. The initial weight loss temperature in air of the film by thermogravimetric analysis (TGA) was found to be about 400° C. at 15° C./minute. The linear coefficient of thermal expansion by thermomechanical analysis (TMA) at 10° C./minute from 0° to 200° C. was found to be 70 ppm. The dried film also exhibited a dielectric constant of 2.3 at 1 MHz. A thin film of the polyimide (3 micron) on a quartz crystal (heating profile as above) had a moisture absorption of only 0.6% at 85% RH when measured on a microbalance.

EXAMPLE 10

Into a 100 ml reaction kettle equipped with a mechanical stirrer and nitrogen inlet and outlet, were charged 6.1728 g (13.2373 mmole) of PXDA and 5.8272 g (13.2373 mmole) of RfbMPD. The monomers were dissolved in 28 ml of NMP and allowed to react overnight at room temperature to produce a viscous poly(amic acid) solution. Afterwards, 10 ml (10.81 g, 105.90 mmole) of acetic anhydride and 7.5 ml (7.33 g, 92.66 mmole) of pyridine were added successively. After about 1 hour of reaction, 8 ml of NMP were added to dilute the very viscous reaction mixture. The reaction was allowed to proceed for an additional 6 hours and then was further diluted with 12 ml of NMP. It was then precipitated into methanol to yield a white fibrous product which after filtration and drying was redissolved in chloroform and precipitated into methanol and again filtered and dried under vacuum with nitrogen bleed. H-NMR in CDCl3 was consistent with the proposed polyimide structure with resonances at 7.85 ppm (singlet), 7.55 ppm (singlet), and 7.4 (multiplet) due to the aromatic protons of PXDA moieties, and resonances at 7.65 ppm, 7.48 ppm (aromatic) and 3.6 ppm (methylene) due to RfbMPD moieties. The polymer was subsequently dissolved in tetrachloroethane (TCE) and filtered through an 1 micron filter. It was then spin coated onto silicon wafers, prebaked at 135° C. in air for 30 minutes, and then heated in a nitrogen oven from room temperature to 200° C. and held for 30 minutes and then heated to 350° C. and held at 350° C. for one hour. The resulting 13.6 micron, almost colorless polyimide film had the following tensile properties when measured on an Instron Model 4501 at a crosshead speed of 5.080 mm/minute: Tensile strength at break=115 MPa, Elongation at break=25%, Young's modulus=1.9 GPa. The dried film also exhibited a dielectric constant of 2.4 at 1 MHz.

What is claimed is:
1. A perfluorinated amine of the formula:

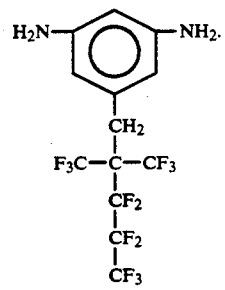

2. A perfluorinated amine of the formula:

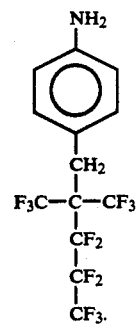

* * * * *